(12) United States Patent
Ludolph et al.

(10) Patent No.: US 11,981,619 B2
(45) Date of Patent: May 14, 2024

(54) ALKOXYLATED ESTERAMINES AND SALTS THEREOF

(71) Applicant: BASF SE, Ludwigshafen am Rhein (DE)

(72) Inventors: Bjoern Ludolph, Ludwigshafen am Rhein (DE); Sophia Ebert, Ludwigshafen am Rhein (DE); Christian Bittner, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 16/624,956

(22) PCT Filed: Jun. 26, 2018

(86) PCT No.: PCT/EP2018/067047
§ 371 (c)(1),
(2) Date: Dec. 20, 2019

(87) PCT Pub. No.: WO2019/007750
PCT Pub. Date: Jan. 10, 2019

(65) Prior Publication Data
US 2020/0188257 A1  Jun. 18, 2020

(30) Foreign Application Priority Data

Jul. 7, 2017 (EP) ..................... 17180161

(51) Int. Cl.
| | | |
|---|---|---|
| C07C 229/08 | (2006.01) | |
| A61K 8/41 | (2006.01) | |
| A61K 8/44 | (2006.01) | |
| A61Q 5/02 | (2006.01) | |
| A61Q 19/10 | (2006.01) | |
| C07C 227/18 | (2006.01) | |
| C08G 59/52 | (2006.01) | |
| C11D 3/33 | (2006.01) | |

(52) U.S. Cl.
CPC .............. *C07C 229/08* (2013.01); *A61K 8/41* (2013.01); *A61K 8/44* (2013.01); *A61Q 5/02* (2013.01); *A61Q 19/10* (2013.01); *C07C 227/18* (2013.01); *C08G 59/52* (2013.01); *C11D 3/33* (2013.01)

(58) Field of Classification Search
None
See application file for complete search history.

(56) References Cited

U.S. PATENT DOCUMENTS

| | | | |
|---|---|---|---|
| 6,346,643 B1 | 2/2002 | Lele et al. | |
| 8,709,450 B2 * | 4/2014 | Kaneko | A61L 31/145 536/56 |
| 8,735,332 B2 | 5/2014 | Leinweber et al. | |
| 2010/0330004 A1 | 12/2010 | Burgo | |
| 2015/0273108 A1 | 10/2015 | Askari et al. | |

FOREIGN PATENT DOCUMENTS

| | | | |
|---|---|---|---|
| CN | 104645348 A | 5/2015 | |
| DE | 2025629 A1 | 12/1971 | |
| EA | 023366 B1 | 5/2016 | |
| EP | 2000460 A1 | 12/2008 | |
| EP | 2172508 A1 | 4/2010 | |
| EP | 2360203 A1 | 8/2011 | |
| EP | 2588437 A1 | 5/2013 | |
| JP | 2003064282 A | 3/2003 | |
| JP | 2005263890 A | 9/2005 | |
| JP | 2014-062193 A | 4/2014 | |
| JP | 2014-070093 A | 4/2014 | |
| JP | 2015-516240 A | 6/2015 | |
| KR | 1710186 B1 * | 3/2017 | ............... A61K 8/44 |
| WO | WO-2003059317 A2 | 7/2003 | |
| WO | WO-2007054226 A1 | 5/2007 | |

(Continued)

OTHER PUBLICATIONS

Flach et al., Colloid and Polymer Science (1996), 274(3), pp. 261-268.*
International Search Report for PCT/EP2018/067047 dated Sep. 27, 2018.
International Search Report for PCT/EP2018/067111 dated Oct. 1, 2018.
Written Opinion of the International Searching Authority for PCT/EP2018/067047 dated Sep. 27, 2018.
Written Opinion of the International Searching Authority for PCT/EP2018/067111 dated Oct. 1, 2018.
U.S. Appl. No. 16/624,964, filed Dec. 20, 2019, Ludolph et al.
European Search Report for EP Patent Application No. 17180161.6, dated Jan. 24, 2018, 3 pages.

(Continued)

*Primary Examiner* — Brian J Davis
(74) *Attorney, Agent, or Firm* — Faegre Drinker Biddle & Reath LLP

(57) ABSTRACT

The present invention relates to alkoxylated esteramines of Formula (I) and salts thereof. Esteramines according to the present invention may be used in cleaning composition, for example in liquid laundry detergents. They lead to improved cleaning performance of said compositions, for example when used in cold water washing conditions. They surprisingly boost grease cleaning performance of liquid laundry detergents, especially under cold water washing conditions. Whiteness is also improved. The esteramine according to the present invention show improved compatibility in liquid laundry detergent formulations.

17 Claims, No Drawings

(56) References Cited

FOREIGN PATENT DOCUMENTS

WO        2012/005897 A1     1/2012
WO        2014/158288 A1    10/2014

OTHER PUBLICATIONS

William Reusch, "Proteins, Peptides and Amino Acids", XP002777120, May 5, 2013, 10 pages.
Boekhoven, et al., "Size control and compartmentalization in self-assembled nano-structures of a multisegment amphiphile", Chemical Communications, vol. 46, Issue 20, Apr. 7, 2010, pp. 3490-3492.
Osanai, et al., "Preparation and antimicrobial properties of polyoxyethylene monoalkyl ether glycinates and alaninates.", Effects of oxyethylene group on the antimicrobial properties, Bokin Bobai, vol. 15, Issue 4, 1987, pp. 157-162.
"7.2.4. The choice of emulsifier and characterization of the emulsifying properties of surfactants", retrieved on Aug. 2, 2023, URL-https://xumuk.ru/colloidchem/191.html., pp. 6.

\* cited by examiner

ALKOXYLATED ESTERAMINES AND SALTS THEREOF

CROSS-REFERENCE TO RELATED APPLICATIONS

This application is a national stage application (under 35 U.S.C. § 371) of PCT/EP2018/067047, filed Jun. 26, 2018, which claims benefit of European Application No. 17180161.6, filed Jul. 7, 2017, both of which are incorporated herein by reference in their entirety.

The invention relates to alkoxylated esteramines and salts thereof.

Due to the increasing popularity of easy-care fabrics made of synthetic fibers as well as the increasing energy costs and growing ecological concerns of detergent users, the once popular hot water wash has now taken a back seat to washing fabrics in cold water. Many commercially available laundry detergents are even advertised as being suitable for washing fabrics at 40° C. or 30° C. or even at room temperature. To achieve satisfactory washing result at such low temperatures, i.e. results comparable to those obtained with hot water washes, the demands on low temperature detergents are especially high.

It is known to include certain additives in detergent compositions to enhance the detergent power of conventional surfactants so as to improve the removal of grease stains at temperatures of 60° C. and below.

U.S. Pat. No. 6,346,643 discloses a process for the preparation of esters of poly(ethylene glycol) with amino acid hydrochlorides.

DE 2025629 discloses esters of glutamic acid and $C_{10}$ to $C_{18}$ fatty alcohols and derivatives.

WO 2007/054226 describes the use of pyroglutamic acid esters as gas hydrate inhibitors. The pyroglutamic acid esters are obtained by esterification of pyroglutamic acid or glutamic acid with an alcohol comprising 1 to 100 hydroxyl groups.

JP2003064282 discloses ligands for semiconductor particles based on triethylene glycol $C_1$ to $C_7$ monoethers esterified with $C_2$ to $C_{21}$ aminoacids.

JP2005263890 discloses esters of $C_6$ to $C_{10}$ ζ- to k-amino acids of ethoxylated glycerols.

WO2003059317 describes polyethylene glycocl monomethyl or -ethyl ethers esterified with alpha-aminoacids as part of a medicinal aerosol composition.

There is a continuous need for cleaning compositions that remove grease stains from fabrics and other soiled materials, as grease stains are challenging stains to remove. Conventional cleaning compositions directed to grease removal frequently utilize various amine compounds which tend to show strong negative impacts on whiteness. As a consequence there is still a continual need for amine compounds which provide grease removal abilities from fabrics and other soiled materials which at the same time do not negatively impact clay cleaning abilities or whiteness. There is a need for compounds having grease cleaning abilities at low temperatures.

It was an object of the present invention to provide compounds which comply with the above identifies objectives and needs.

This goal was achieved by the present invention as described herein below and as reflected in the claims.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim.

In each instance herein any of the terms "comprising", "consisting essentially of" and "consisting of" may be replaced with either of the other two terms.

Generally, as used herein, the term "obtainable by" means that corresponding products do not necessarily have to be produced (i.e. obtained) by the corresponding method or process described in the respective specific context, but also products are comprised which exhibit all features of a product produced (obtained) by said corresponding method or process, wherein said products were actually not produced (obtained) by such method or process. However, the term "obtainable by" also comprises the more limiting term "obtained by", i.e. products which were actually produced (obtained) by a method or process described in the respective specific context.

The present invention relates to alkoxylated esteramines of Formula (I) and salts thereof,

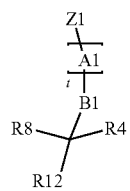

(Formula I)

wherein independently from each other t being an integer from 1 to 100;

$A_1$ is independently for each repetition unit t selected from the list consisting of ethyleneoxy group, 1,2-propyleneoxy group, 1,2-butyleneoxy group, 2,3-butyleneoxy group, i-butyleneoxy group, pentyleneoxy group, hexyleneoxy group, styryloxy group, decenyloxy group, dodecenyloxy group, tetradecenyloxy group, and hexadecanyloxy group, wherein for t equal to 1 the oxygen atom of the $A_1$ group is bound to the B group and the following $A_1$ group is always bound via the oxygen atom to the previous $A_1$ group.

$B_1$ is independently selected from the group consisting of a bond, linear $C_1$ to $C_{12}$ alkanediyl groups, and branched $C_1$ to $C_{12}$ alkanediyl groups;

$R_4$, $R_8$, and $R_{12}$ being selected from the group consisting of H, linear alkyl, branched alkyl, and cycloalkyl;

with the provisio that $Z_1$ is selected from the group consisting of alanine, arginine, asparagine, aspartic acid, cysteine, glutamine, glycine, histidine, isoleucine, leucine, lysine, methionine, phenylalanine, proline, serine, threonine, tryptophan, tyrosine, valine, and a compound according to Formula (II), wherein said compound according to Formula (II) connects to the compound according to Formula (I) via the bond labeled with *, with the provisio of at least one group $R_4$, $R_8$, and/or $R_{12}$ containing at least 7 or more carbon atoms;

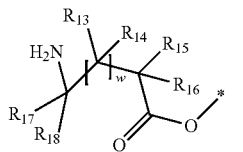

(Formula II)

with independently from each other
w being an integer from 0 to 12;
$R_{13}$ and $R_{14}$ independently for each repetition unit w being selected from the group consisting of H, linear alkyl, branched alkyl, and cycloalkyl;
$R_{15}$, $R_{16}$, $R_{17}$, and $R_{18}$ being selected from the group consisting of H, linear alkyl, branched alkyl, and cycloalkyl.

Esteramines according to the present invention may be used in cleaning composition, for example in liquid laundry detergents. They lead to improved cleaning performance of said compositions, for example when used in cold water washing conditions. They surprisingly boost grease cleaning performance of liquid laundry detergents, especially under cold water washing conditions. The esteramine according to the present invention show improved compatibility in liquid laundry detergent formulations.

In the following, the various embodiments of the present invention are described in more detail:

$A_1$ is independently for each repetition unit t selected from the list consisting of ethyleneoxy group, 1,2-propyleneoxy group, 1,2-butyleneoxy group, 2,3-butyleneoxy group, i-butyleneoxy group pentenyloxy group, hexyloxy group, styryloxy group, decenyloxy group, dodecyloxy group, tetradecenyloxy group and hexadecenyloxy group, wherein for t equal to 1 the oxygen atom of the $A_1$ group is bound to the B group and the following $A_1$ groups are always bound via the oxygen atom to the previous $A_1$ group. When t is equal to or more than 2, the independently selected $A_1$ either form a randomly distributed sidechain of various alkylenyloxy units or the form a block structure with at least one alkylenyloxy group repeating itself at least two times, optionally followed by further blocks of different alkylenyloxy group repeating themselves at least two times.

In one embodiment $A_1$ is independently for each repetition unit t selected from the list consisting of ethylenoxy group, 1,2-propyleneoxy group 1,2-1,2-propyleneoxy group, and 1,2-butylenoxy group. In another embodiment, $A_1$ forms a block of at least two ethyleneoxy groups followed by a block of at least two propylenoxy groups, optionally followed by another block of at least two ethyleneoxy groups. In another embodiment, $A_1$ forms a block of at least two 1,2-propyleneoxy groups followed by a block of at least two ethylenoxy groups, optionally followed by another block of at least two 1,2-propyleneoxy groups. In another embodiment, $A_1$ is selected from the list consisting of ethyleneoxy group, 1,2-propyleneoxy group, and 1,2-butyleneoxy group in such a way that at least one block of ethyleneoxy groups, 1,2-propyleneoxy groups, or 1,2-butyleneoxy groups is formed, optionally followed by one or more blocks of ethyleneoxy groups, 1,2-propyleneoxy groups, or 1,2-butyleneoxy groups. In another embodiment, $A_1$ is ethyleneoxy groups. In another embodiment, $A_1$ is 1,2-propyleneoxy groups. In another embodiment, $A_1$ is selected in such a way that a block of one to five ethylenoxy groups is followed by a block of one to three propylenoxy groups followed by a block of one to five ethylenoxy groups.

In one embodiment t is in the range of from 1 to 30. In another embodiment t is in the range of from 1 to 20. In another embodiment t is in the range of from 2 to 10.

In one embodiment of the present invention, $B_1$ is selected from the group consisting of a bond, and linear $C_1$ to $C_{12}$ alkanediyl groups. In another embodiment, $B_1$ is selected from the group consisting of a bond, and linear $C_1$ to $C_6$ alkanediyl groups. In another embodiment, $B_1$ is selected from the group consisting of a bond, and linear $C_1$ to $C_3$ alkanediyl groups. In another embodiment, $B_1$ is selected from the group consisting of a bond, and a $C_1$ alkanediyl group. In another embodiment $B_1$ is selected from the group consisting of a bond, and a $C_1$ alkanediyl group. In another embodiment $B_1$ is bond.

In one embodiment of the present invention, $R_4$, $R_8$, and $R_{12}$ are all independently selected from the group consisting of H, linear alkyl, branched alkyl, and cycloalkyl. In one embodiment, $R_4$, $R_8$, and $R_{12}$ are all independently selected from the group consisting of H, linear $C_1$ to $C_{12}$ alkyl, and $C_1$ to $C_{12}$ branched alkyl. In another embodiment, $R_4$, $R_8$, and $R_{12}$ are all independently selected from the group consisting of H, linear $C_1$ to $C_6$ alkyl, and $C_1$ to $C_9$ branched alkyl.

For $Z_1$ being selected a compound according to Formula (II), said compound according to Formula (II) connects to the compound of Formula (I) via the bond labeled with *,

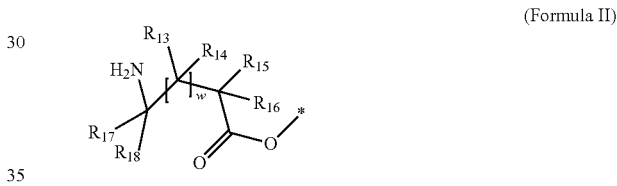

(Formula II)

with independently from each other
w being an integer from 0 to 12;
$R_{13}$ and $R_{14}$ independently for each repetition unit w being selected from the group consisting of H, linear alkyl, branched alkyl, and cycloalkyl;
$R_{15}$, $R_{16}$, $R_{17}$, and $R_{18}$ being selected from the group consisting of H, linear alkyl, branched alkyl, and cycloalkyl. In one embodiment of the present invention, $R_{13}$, $R_{14}$, $R_{15}$, $R_{16}$, $R_{17}$, and Rig are all independently selected from the group consisting of H, linear $C_1$ to $C_{12}$ alkyl, and $C_1$ to $C_{12}$ branched alkyl. In another embodiment, $R_{13}$, $R_{14}$, $R_{15}$, $R_{16}$, $R_{17}$, and $R_{18}$ are all independently selected from the group consisting of H, linear $C_1$ to $C_6$ alkyl, and $C_1$ to $C_9$ branched alkyl.

In one embodiment of the present invention $Z_1$ is selected from the group consisting of alanine, glycine, lysine, and of compounds according to Formula (II), wherein w is an integer in the range of from 1 to 4, and the compound according to Formula (II) connects to the compound according to Formula (I) via the bond labeled with *, with the proviso of at least one group $R_4$, $R_8$, and/or $R_{12}$ containing at least 7 or more carbon atom. In another embodiment $Z_1$ is alanine. In another embodiment $Z_1$ is a compound according to Formula (II) with w=0 and $R_{15}$ to $R_{18}$ are all H. In another embodiment $Z_1$ is a compound according to Formula (II) with w=1 and $R_{13}$ to $R_{18}$ are all H. In another embodiment $Z_1$ is a compound according to Formula (II) with w=3 and $R_{13}$ to $R_{18}$ are all H.

In another embodiment of the present invention $B_1$ is selected from branched or linear $C_1$- to $C_{12}$-alkyl and $R_8$ is selected from linear or branched $C_6$- to $C_{23}$-alkyl. In another embodiment of the present invention $B_1$ is selected from branched or linear $C_1$- to $C_{12}$-alkyl and $R_8$ is selected from linear or branched $C_1$- to $C_3$-alkyl. Another embodiment consists of $B_1$ being 2-ethyl-ethandiyl and $R_8$ being linear $C_3$-alkyl.

In another embodiment of the present invention $B_1$ is selected from branched or linear $C_1$- to $C_{12}$-alkyl and $R_8$ is selected from linear or branched $C_1$- to $C_3$-alkyl, and $Z_1$ is a is a compound according to Formula (II) with w=3 and $R_{13}$ to $R_{18}$ are all H.

In another embodiment of the present invention $B_1$ is selected from branched or linear $C_6$- to $C_{12}$-alkyl and $R_8$ is selected from linear or branched $C_1$- to $C_3$-alkyl, t is in the range of from 1 to 10, $A_1$ is for each repetition unit t ethyleneoxy group, and $Z_1$ is selected from the group consisting of alanine, a compound according to Formula (II) with w=0 and $R_{15}$ to $R_{18}$ all H, a compound according to Formula (II) with w=1 and $R_{13}$ to $R_{18}$ all H, and a compound according to Formula (II) with w=3 and $R_{13}$ to $R_{18}$ all H.

In another embodiment of the present invention $B_1$ is selected from branched or linear $C_6$- to $C_{12}$-alkyl and $R_8$ is selected from linear or branched $C_1$- to $C_3$-alkyl, $R_4$ and $R_{12}$ are selected from H and linear or branched $C_1$- to $C_3$-alkyl, t is in the range of from 1 to 10, $A_1$ is for each repetition unit t 1,2-propyleneoxy group, and $Z_1$ is selected from the group consisting of alanine, a compound according to Formula (II) with w=0 and $R_{15}$ to $R_{18}$ all H, a compound according to Formula (II) with w=1 and $R_{13}$ to $R_{18}$ all H, and a compound according to Formula (II) with w=3 and $R_{13}$ to $R_{18}$ all H.

The esteramines according to the present invention are obtained either as free amines, as salts thereof or as a mixture of free amines and salts. Salts are formed by at least partial protonation of the amine groups by an acid being a protic organic acid or a protic inorganic acid. In one embodiment, the acid for at least partial protonation of the amine groups is selected from the group consisting of methanesulfonic acid, hydrochloric acid, hydrobromic acid, sulfuric acid, phosphoric acid, citric acid, and lactic acid. In one embodiment, the acid is selected from the group of methanesulfonic acid, hydrochloric acid, and sulfuric acid. In another embodiment, the acid is methanesulfonic acid.

Partial protonation in one embodiment is protonation of the amine groups in the range of from 1 to 99 mol-% of all amine groups, in another embodiment in the range of from 10 to 90 mol-% of all amine groups, in another embodiment in the range of from 25 to 85 mol-%, in another embodiment in the range of from 40 to 75 mol-% of all amine groups.

The present invention also comprises combinations of at least two embodiments as presented herein.

The present invention also relates to a process for preparation of esteramine or salt thereof comprises the steps of
a) Alkoxylation of an alcohol of Formula (III)

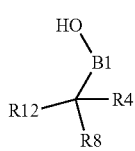

Formula (III)

wherein independently from each other
$B_1$ is selected from the group consisting of a bond, linear $C_1$ to $C_{12}$ alkanediyl groups, and branched $C_1$ to $C_{12}$ alkanediyl groups;

$R_4$, $R_8$, and $R_{12}$ being selected from the group consisting of H, linear alkyl, branched alkyl, and cycloalkyl;
with one or more $C_2$ to 016 alkylene oxide, followed by
b) at least partial esterification of the alkoxylated alcohol with at least one acid selected from the group consisting of alanine, arginine, asparagine, aspartic acid, cysteine, glutamine, glycine, histidine, isoleucine, leucine, lysine, methionine, phenylalanine, proline, serine, threonine, tryptophan, tyrosine, valine, and acids of Formula (IV)

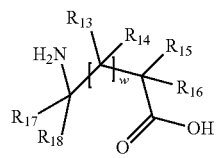

(Formula IV)

with w being an integer from 0 to 12,
$R_{13}$ and $R_{14}$ independently for each repetition unit w being selected from the group consisting of H, linear alkyl, branched alkyl, and cycloalkyl;
$R_{15}$, $R_{16}$, $R_{17}$, and Rig being selected from the group consisting of H, linear alkyl, branched alkyl, and cycloalkyl.

In one embodiment of the present invention, $B_1$ is selected from the group consisting of a bond, and linear $C_u$ to $C_{12}$ alkanediyl groups. In another embodiment, $B_1$ is selected from the group consisting of a bond, and linear $C_1$ to $C_6$ alkanediyl groups. In another embodiment, $B_1$ is selected from the group consisting of a bond, and linear $C_1$ to $C_3$ alkanediyl groups. In another embodiment, $B_1$ is selected from the group consisting of a bond, and a $C_1$ alkanediyl group. In another embodiment $B_1$ is a bond.

In one embodiment of the present invention, $R_4$, $R_8$, and $R_{12}$ are all independently selected from the group consisting of H, linear alkyl, branched alkyl, and cycloalkyl. In one embodiment, $R_4$, $R_8$, and $R_{12}$ are all independently selected from the group consisting of H, linear $C_1$ to $C_{12}$ alkyl, and $C_1$ to $C_{12}$ branched alkyl. In another embodiment, $R_4$, $R_8$, and $R_{12}$ are all independently selected from the group consisting of H, linear $C_1$ to $C_6$ alkyl, and $C_1$ to $C_9$ branched alkyl.

Step a) Alkoxylation of Alcohol According to Formula (III) with at Least One $C_2$- to $C_{16}$-Akylene Oxide.

The alcohol of Formula (III) may be reacted with one single $C_2$- to $C_{16}$-alkylene oxide or combinations of two or more different $C_2$- to $C_{16}$-alkylene oxides. Using two or more different $C_2$- to $C_{16}$-alkylene oxides, the resulting polymer can be obtained as a block-wise structure or a random structure.

The molar ratio of alcohol of Formula (III) to total alkylene oxide may be in the range of from 1:1 to 1:400. In one embodiment, the molar ratio of the moles of hydroxyl groups of the alcohol of Formula (III) to the alkylene oxides with which the alkoxylation reaction is carried out may lie in the range of 1:1 to 1:100. In another embodiment the ratio of the moles of hydroxyl groups of the alcohol of Formula (III) to the alkylene oxides at which the alkoxylation reaction is carried out may lie in the range of from 1:2 to 1:50, in another embodiment in the range of 1:3 to 1:10.

This reaction may be undertaken generally in the presence of a catalyst at a reaction temperature from about 70 to about 200° C., in another embodiment from about 80 to about 160° C. This reaction may be affected at a pressure of up to about 10 bar, in another embodiment at a pressure of up to about 8 bar.

Examples of suitable catalysts comprise basic catalysts such as alkali metal and alkaline earth metal hydroxides such as sodium hydroxide, potassium hydroxide and calcium hydroxide, alkali metal alkoxides, in particular sodium and potassium $C_1$-$C_4$-alkoxides, such as sodium methoxide, sodium ethoxide and potassium tert-butoxide, alkali metal and alkaline earth metal hydrides such as sodium hydride and calcium hydride, and alkali metal carbonates such as sodium carbonate and potassium carbonate. In one embodiment, alkali metal hydroxides are used. In another embodiment, potassium hydroxide and sodium hydroxide are used. Typical use amounts for the base are from 0.01 to 10% by weight, in particular from 0.05 to 2% by weight, based on the total amount of alcohol and $C_2$- to $C_{16}$-alkylene oxide.

Step b) Esterification

The esterification reaction may be performed as known in the art. An inorganic or organic protic acid may be added to the product of step a). The molar ratio of amino acid to hydroxyl groups of the alkoxylated alcohol of step a) is 0.8:1 to 1:1.5. In one embodiment, the process is carried out with the molar ratio of the acid to the hydroxyl groups of the alkoxylated alcohol of step a) is in the range of from 0.1:1 to 1:1. Reaction temperatures may be from 50° C. to 200° C., in another embodiment from 80° C. to 160° C. The reaction may be affected by applying vacuum from 1000 mbar to 1 mbar, in another embodiment from 500 mbar to 5 mbar. Reaction times may be from 2 to 48 hours. Suitable solvents for the reaction may be water, toluene, xylene.

The effects for laundry as described and exemplified herein may be extrapolated to personal care applications.

The esteramines and salts thereof can be used in applications in personal care, as curing agent for epoxy resins, as reactant in the production of polymers, in polyurethanes, polyureas, or as thermoplastic polyamide adhesives. The can also be used in shampoo or body wash formulations. The esteramines and salts thereof may be included in personal care composition.

Methods $^1$H NMR measured in MeOD with Bruker Avance 400 MHz spectrometer.

pH is measured in 10% aqueous solution.

Hydroxyl values are measured according to DIN 53240-1. Molecular weight of polyalkylene oxides (e.g. polyethylene glycol) is calculated from the measured hydroxyl values by following formula:

Molecular weight[g/mol]=1000/(hydroxyl value[mg-KOH/g]/56.11)×hydroxyl groups per molecule

EXAMPLES

Example 1: 2-Propylheptanol, Ethoxylated with 3 Mole Ethylene Oxide, Ester with 6-Amino Hexane Acid, Methane Sulfonic Acid Salt In a 4-neck vessel with thermometer, reflux condenser, nitrogen inlet, dropping funnel, and stirrer, 58.1 g 2-Propylheptanol, ethoxylated with 3 mole ethylene oxide and 26.2 g 6-amino hexane acid are placed and heated to 90° C. To the mixture 19.6 g methane sulfonic acid is added within 10 minutes. The reaction mixture is heated to 130° C. and is stirred for 0.5 hours at 130° C. Vacuum (2 mbar) is applied and the reaction mixture is stirred for additional 10 hours at 130° C. 90.5 g of a light brown solid is obtained. $^1$H-NMR in MeOD indicates complete conversion to 6-amino hexane acid acid—triethylene glycol 2-propyl-heptylether ester as methane sulfonic acid salt.

Example 2: $C_{13}$—Oxoalkohol Ethoxylated with 3 Mole Ethylene Oxide, Ester with 6-Amino Hexane Acid, Methane Sulfonic Acid Salt In a 4-neck vessel with thermometer, reflux condenser, nitrogen inlet, dropping funnel, and stirrer, 65.93 g $C_{13}$ oxoalkohol ethoxylated with 3 mole ethylene oxide and 26.23 g 6-amino hexane acid are placed and heated to 90° C. To the mixture 19.6 g methane sulfonic acid is added within 10 minutes. The reaction mixture is heated to 135° C. and is stirred for 7.0 hours at 135° C. Vacuum (5 mbar) is applied and the reaction mixture is stirred for additional 3 hours at 130° C. 101.95 g of a light brown solid is obtained. $^1$H-NMR in MeOD indicates complete conversion to 6-amino hexane acid acid—triethylene glycol $C_{13}$-oxoalkohol ester as methane sulfonic acid salt.

Example 3

3a: C12/C14 fatty alcohol, alkoxylated with 2 mol propylene oxide and 2 mol ethylene oxide In a 2 l autoclave 573.6 g C12/C14 fatty alcohol and 2.4 g potassium tert.-butylate are placed and the mixture is heated to 140° C. The vessel is purged three times with nitrogen and 348.5 g propylene oxide is added within 5 h. The mixture is stirred for additional 6 h, followed by the addition of 264.3 g ethylene oxide within 5 h. To complete the reaction, the mixture is allowed to post-react for additional 6 h at 140° C. The reaction mixture was stripped with nitrogen and volatile compounds were removed in vacuo at 80° C. After filtration 1178.0 g of a light yellowish oil was obtained (hydroxy value: 141.8 mgKOH/g).

3b: C12/C14 fatty alcohol, alkoxylated with 2 mol propylene oxide and 2 mol ethylene oxide, ester with 6-amino hexane acid, methane sulfonic acid salt In a 4-neck vessel with thermometer, reflux condenser, nitrogen inlet, dropping funnel, and stirrer, 59.3 g C12/C14 fatty alcohol, alkoxylated with 2 mol propylene oxide and 2 mol ethylene oxide and 17.9 g 6-amino hexane acid are placed and heated to 60° C. To the mixture 13.4 g methane sulfonic acid is added within 10 minutes. The temperature is allowed to rise to 70° C. during the addition. The reaction mixture is heated to 130° C. and is stirred for 13 hours at 130° C. Volatile compounds are removed in vacuo (2 mbar) at elevated temperature (135° C.) and 81.0 g of a light brown solid is obtained. $^1$H-NMR in MeOD indicates complete conversion to $C_{12}/C_{14}$ fatty alcohol, alkoxylated with 2 mol propylene oxide and 2 mol ethylene oxide, ester with 6-amino hexane acid, methane sulfonic acid salt.

Example 4

4a 2-ethyl-hexanol, alkoxylated with 2 mol propylene oxide and 2 mol ethylene oxide In a 2 l autoclave 390.7 g 2-ethylhexanol and 2.0 g potassium tert.-butylate are placed and the mixture is heated to 140° C. The vessel is purged three times with nitrogen and 348.5 g propylene oxide is added within 4 h. The mixture is stirred for additional 6 h, followed by the addition of 264.3 g ethylene oxide within 3 h. To complete the reaction, the mixture is allowed to post-react for additional 6 h at 140° C. The reaction mixture was stripped with nitrogen and volatile compounds were removed in vacuo at 80° C. 1024.0 g of a light yellowish oil was obtained (hydroxy value: 164.0 mgKOH/g).

4b: 2-ethylhexanol, alkoxylated with 2 mol propylene oxide and 2 mol ethylene oxide, ester with 6-amino hexane acid, methane sulfonic acid salt In a 4-neck vessel with thermometer, reflux condenser, nitrogen inlet, dropping funnel, and stirrer, 50.2 g 2-ethylhexanol, alkoxylated with 2 mol propylene oxide and 2 mol ethylene oxide and 17.9 g 6-amino hexane acid are placed and heated to 60° C. To the mixture 13.4 g methane sulfonic acid is added within 10 minutes. The temperature is allowed to rise to 70° C. during the addition. The reaction mixture is heated to 130° C. and is stirred for 13 hours at 130° C. Volatile compounds are removed in vacuo (2 mbar) at elevated temperature (135° C.) and 72.0 g of a light brown solid is obtained. $^1$H-NMR in MeOD indicates complete conversion to 2-ethylhexanol, alkoxylated with 2 mol propylene oxide and 2 mol ethylene oxide, ester with 6-amino hexane acid, methane sulfonic acid salt.

Example 5

5a: 2-propylheptanol, alkoxylated with 2 mol propylene oxide and 2 mol ethylene oxide In a 2 l autoclave 474.0 g 2-ethylhexanol and 2.4 g potassium tert.-butylate are placed and the mixture is heated to 140° C. The vessel is purged three times with nitrogen and 348.5 g propylene oxide is added within 4 h. The mixture is stirred for additional 6 h, followed by the addition of 264.3 g ethylene oxide within 3 h. To complete the reaction, the mixture is allowed to post-react for additional 6 h at 140° C. The reaction mixture was stripped with nitrogen and volatile compounds were removed in vacuo at 80° C. 1065.0 g of a light yellowish oil was obtained (hydroxy value: 152.0 mgKOH/g).

5b: 2-propylheptanol, alkoxylated with 2 mol propylene oxide and 2 mol ethylene oxide, ester with 6-amino hexane acid, methane sulfonic acid salt In a 4-neck vessel with thermometer, reflux condenser, nitrogen inlet, dropping funnel, and stirrer, 59.8 g 2-propylheptanol, alkoxylated with 2 mol propylene oxide and 2 mol ethylene oxide and 19.7 g 6-amino hexane acid are placed and heated to 60° C. To the mixture 14.7 g methane sulfonic acid is added within 10 minutes. The temperature is allowed to rise to 70° C. during the addition. The reaction mixture is heated to 130° C. and is stirred for 5 hours at 130° C. Then, vacuum is applied (800 mbar) and the mixture is stirred for 2 hours under these conditions. Volatile compounds are removed in vacuo (2 mbar) at elevated temperature (140° C.) and 86.9 g of a light brown solid is obtained. $^1$H-NMR in MeOD indicates complete conversion to 2-propylheptanol, alkoxylated with 2 mol propylene oxide and 2 mol ethylene oxide, ester with 6-amino hexane acid, methane sulfonic acid salt.

Example 6

6a: 2-ethyl-hexanol, ethoxylated with 1 mol ethylene oxide

In a 2 l autoclave 651.1 g 2-ethylhexanol and 1.74 g potassium tert.-butylate are placed and the mixture is heated to 140° C. The vessel is purged three times with nitrogen and 220.3 g ethylene oxide is added within 4 h. The mixture is stirred for additional 5 h at 140° C. to complete the reaction. The reaction mixture was stripped with nitrogen and volatile compounds were removed in vacuo at 80° C. 870.0 g of a light yellowish oil was obtained (hydroxy value: 321.0 mgKOH/g).

6b: 2-ethylhexanol, ethoxylated with 1 mol ethylene oxide, ester with 6-amino hexane acid, methane sulfonic acid salt In a 4-neck vessel with thermometer, reflux condenser, nitrogen inlet, dropping funnel, and stirrer, 38.3 g 2-ethylhexanol, ethoxylated with 1 mol ethylene oxide and 26.2 g 6-amino hexane acid are placed and heated to 60° C. To the mixture 19.6 g methane sulfonic acid is added within 10 minutes. The temperature is allowed to rise to 70° C. during the addition. The reaction mixture is heated to 130° C. and is stirred for 4 hours at 130° C. Vacuum is applied and volatile compounds are removed in vacuo (5 mbar) at elevated temperature (135° C.) for 2 hours. 72.0 g of a light brown solid is obtained. $^1$H-NMR in MeOD indicates complete conversion to 2-ethylhexanol, ethoxylated with 1 mol ethylene oxide, ester with 6-amino hexane acid, methane sulfonic acid salt.

Example 7

7a: 2-propylheptanol, ethoxylated with 1 mol ethylene oxide

In a 2 l autoclave 794.0 g 2-propylheptanol and 2.0 g potassium tert.-butylate are placed and the mixture is heated to 140° C. The vessel is purged three times with nitrogen and 220.9 g ethylene oxide is added within 4 h. The mixture is stirred for additional 5 h at 140° C. to complete the reaction. The reaction mixture was stripped with nitrogen and volatile compounds were removed in vacuo at 65° C. 1010.0 g of a light yellowish oil was obtained (hydroxy value: 275.0 mg KOH/g).

7b: 2-propylheptanol, ethoxylated with 1 mol ethylene oxide, ester with 6-amino hexane acid, methane sulfonic acid salt In a 4-neck vessel with thermometer, reflux condenser, nitrogen inlet, dropping funnel, and stirrer, 44.5 g 2-propylheptanol, ethoxylated with 1 mol ethylene oxide and 26.2 g 6-amino hexane acid are placed and heated to 60° C. To the mixture 19.6 g methane sulfonic acid is added within 10 minutes. The temperature is allowed to rise to 70° C. during the addition. The reaction mixture is heated to 130° C. and is stirred for 4 hours at 130° C. Vacuum is applied and volatile compounds are removed in vacuo (4 mbar) at elevated temperature (135° C.) for 6 hours. 80.0 g of a light brown solid is obtained. $^1$H-NMR in MeOD indicates complete conversion to 2-propylheptanol, ethoxylated with 1 mol ethylene oxide, ester with 6-amino hexane acid, methane sulfonic acid salt.

Comparative Example 1: Butyltriglycol Ester with 6-Amino Hexane Acid, Methane Sulfonic Acid Salt In a 4-neck vessel with thermometer, reflux condenser, nitrogen inlet, dropping funnel, and stirrer, 64.39 g butyltriglycol and 39.35 g 6-amino hexane acid are placed and heated to 90° C. To the mixture 29.4 g methane sulfonic acid is added within 10 minutes. The reaction mixture is heated to 135° C. and is stirred for 4 hours at 135° C. Vacuum (5 mbar) is applied and the reaction mixture is stirred for additional 13.5 hours at 130° C. 122.0 g of a light brown solid is obtained. $^1$H-NMR in MeOD indicates complete conversion to 6-amino hexane acid acid butyltriglycol ester as methane sulfonic acid salt.

Comparative Example 2: Polyethylene Glycol, $M_w$ Approx. 200 g/Mol; Ester with 6-Amino Hexane Acid, Methane Sulfonic Acid Salt In a 4-neck vessel with thermometer, reflux condenser, nitrogen inlet, dropping funnel, and stirrer, 30.0 g polyethylene glycol ($M_w$ approx. 200 g/mol) and 39.35 g 6-amino hexane acid are placed and heated to 90° C. To the mixture 29.4 g methane sulfonic acid is added within 10 minutes. The reaction mixture is heated to 135° C. and is stirred for 4 hours at 135° C. Vacuum (5 mbar) is applied and the reaction mixture is stirred for additional 22 hours at 135° C. 97.0 g of a light brown solid is obtained. $^1$H-NMR in MeOD indicates complete conversion to 6-amino hexane acid acid polyethylene glycol ester as methane sulfonic acid salt.

Example 8 Use as Additives in Detergents

Technical stain swatches of blue knitted cotton containing Bacon Grease were purchased from Warwick Equest Ltd. The stains were washed for 30 min in a launder-o-meter (manufactured by SDL Atlas) at room temperature using per canister 500 mL of washing solution, 20 metal balls and ballast fabrics. The washing solution contained 5000 ppm of detergent composition DC1 (table 1). Water hardness was 2.5 mM ($Ca^{2+}$: $Mg^{2+}$ was 4:1). Additives were added to the washing solution of each canister separately and in the amount as detailed below. After addition the pH value was re-adjusted to the pH value of washing solution without additive.

Standard colorimetric measurement was used to obtain L*, a* and b* values for each stain before and after the washing. From L*, a* and b* values the stain level were calculated as color difference ΔE (calculated according to DIN EN ISO 11664-4) between stain and untreated fabric.

Stain removal from the swatches was calculated as follows:

$$\text{Stain Removal Index (SRI)} = \frac{\Delta E_{initial} - \Delta E_{washed}}{\Delta E_{initial}} \times 100$$

$\Delta E_{initial}$=Stain level before washing
$\Delta E_{washed}$=Stain level after washing Stain level corresponds to the amount of grease on the fabric. The stain level of the fabric before the washing ($\Delta E_{initial}$) is high, in the washing process stains are removed and the stain level after washing is smaller ($\Delta E_{washed}$) The better the stains have been removed the lower the value for $\Delta E_{washed}$ will be and the higher the difference will be to $\Delta E_{initial}$. Therefore, the value of stain removal index increases with better washing performance.

TABLE 1

Detergent composition DC1

| Ingredients of liquid detergent composition DC1 | percentage by weight |
|---|---|
| n-$C_{10}$-$C_{13}$-alkylbenzene sulfonic acid | 5.3 |
| coconut $C_{12}$-$C_{18}$ fatty acid | 2.4 |
| sodium laureth sulfate + 2 EO | 7.7 |
| potassium hydroxide | 2.2 |
| C13C15-oxo alcohol + 7 EO | 5.4 |
| 1,2 propylene glycol | 6 |
| ethanol | 2 |
| water pH of detergent composition DC1 = 8.0 | To Balance |

TABLE 2

Washing Experiment with Example 2

| | SRI, Bacon Graese Cleaning |
|---|---|
| Without additive | 26.1 |
| Example 2: $C_{13}$ Oxoalkohol ethoxylated with 3 mole ethylene oxide, ester with 6-amino hexane acid, methane sulfonic acid salt; 0.045 g per wash | 31.9 |
| Example 1: $C_{10}$-Guerbetalkohol (2-Propylheptanol) with 3 mole ethylenoxide, ester with 6-amino hexane acid, methane sulfonic acid salt; 0.046 g per wash | 31.8 |
| Comparitive example 1: Butyltriglycol ester with 6-amino hexane acid, methane sulfonic acid salt; 0.049 g per wash | 28.0 |
| Comparitive example 2: Polyethylenglycol, $M_w$ approx. 200 g/mol; ester with 6-amino hexane acid, methane sulfonic acid salt; 0.057 g per wash | 28.1 |

TABLE 3

Washing Experiment with Example 5b: 2-propylheptanol, alkoxylated with 2 mol propylene oxide and 2 mol ethylene oxide, ester with 6-amino hexane acid, methane sulfonic acid salt

| | SRI, Bacon Graese Cleaning |
|---|---|
| Without additive | 8.5 |
| Example 5b: 2-propylheptanol, alkoxylated with 2 mol propylene oxide and 2 mol ethylene oxide, ester with 6-amino hexane acid, methane sulfonic acid salt; 0.099 g per wash | 17.5 |

Use as Additives in Detergents

Technical stain wfk20D (polyester/cotton 65/35, soil: pigment/sebum) from wfk Testgewebe GmbH, was used. Washing procedure and determination of stain removal index was followed as described above but with 1584 ppm of detergent composition 2 (table 4). The pH of the washing solution prior to washing with and without additives was adjusted in each case to pH=8.0.

TABLE 4

Detergent composition DC2

| Ingredients of liquid detergent composition DC2 | percentage by weight |
|---|---|
| linear $C_{11.8}$-alkylbenzene sulfonic acid | 17.6 |
| C12-C15 alkyl ethoxy (1.8) sulfate | 4.4 |
| C12-C14 alcohol + 9 ethylene oxide | 0.9 |
| C12-C18 fatty acid | 1.1 |
| C12-C14 amine oxide | 0.8 |
| Chelant | 2.8 |
| Solvent | 14.8 |
| brightener | 0.2 |
| sodium hydroxide | 1.9 |
| Water | To Balance |

The invention claimed is:

1. An esteramine salt of Formula (I), (Formula I)

$$\begin{array}{c} Z_1 \\ | \\ A_1 \\ | \\ t \\ | \\ B_1 \\ R_8 \diagdown \diagup R_4 \\ | \\ R_{12} \end{array}$$

wherein independently from each other
t being an integer from 1 to 20;
A$_1$ is independently for each repetition unit t selected from the list consisting of ethyleneoxy group, 1,2-propyleneoxy group, 1,2-butyleneoxy group, 2,3-butyleneoxy group, i-butyleneoxy group, pentyleneoxy group, hexyleneoxy group, styryloxy group, decenyloxy group, dodecenyloxy group, tetradecenyloxy group, and hexadecanyloxy group, wherein for t equal to 1 the oxygen atom of the A$_1$ group is bound to the B$_1$ group and the following A group is always bound via the oxygen atom to the previous A$_1$ group;
B$_1$ is independently from each other selected from the group consisting of a bond, linear C$_1$ to C$_{12}$ alkanediyl groups, and branched C$_1$ to C$_{12}$ alkanediyl groups;
R$_4$, R$_8$, and R$_{12}$ being selected from the group consisting of H, linear alkyl, branched alkyl, and cycloalkyl;
Z$_1$ is selected from the group consisting of alanine, arginine, asparagine, aspartic acid, cysteine, glutamine, glycine, histidine, isoleucine, leucine, lysine, methionine, phenylalanine, proline, serine, threonine, tryptophan, tyrosine, valine, and a compound according to Formula (II), wherein said compound according to Formula (II) connects to the compound according to Formula (I) via the bond labeled with *, with the provisio of at least one group R$_4$, R$_8$, and/or R$_{12}$ containing at least 7 or more carbon atoms;

(Formula II)

$$\begin{array}{c} R_{13} \quad R_{14} \quad R_{15} \\ H_2N \diagdown \diagup \diagdown \diagup R_{16} \\ R_{17} \diagup \quad w \quad \diagdown \diagup ^* \\ R_{18} \quad O \end{array}$$

with independently from each other w being an integer from 0 to 12;
R$_{13}$ and R$_{14}$ independently for each repetition unit w being selected from the group consisting of H, linear alkyl, branched alkyl, and cycloalkyl;
R$_{15}$, R$_{16}$, R$_{17}$, and R$_{18}$ being selected from the group consisting of H, linear alkyl, branched alkyl, and cycloalkyl and
wherein the salt is formed by at least partial protonation of the amine group by methanesulfonic acid.

2. The esteramine salt according to claim 1, wherein A$_1$ is independently for each repetition unit t selected from the list consisting of ethyleneoxy group, 1,2-propyleneoxy group, and 1,2-butyleneoxy group.

3. The esteramine salt according to claim 1, wherein Z$_1$ is selected from the group consisting of alanine, glycine, lysine, and a compound according to Formula (II), wherein w is an integer in the range of from 1 to 4, and wherein the compound according to Formula (II) connects to the compound according to Formula (I) via the bond labeled with *, with the provisio of at least one group R$_4$, R$_8$, and/or R$_{12}$ containing at least 7 or more carbon atoms.

4. A process for preparation of an esteramine, of Formula (I) or salt thereof,

Formula 1

$$\begin{array}{c} Z_1 \\ | \\ A_1 \\ | \\ t \\ | \\ B_1 \\ R_8 \diagdown \diagup R_4 \\ | \\ R_{12} \end{array}$$

wherein independently from each other
t being an integer from 1 to 100;
A$_1$ is independently for each repetition unit t selected from the list consisting of ethyleneoxy group, 1,2-propyleneoxy group, 1,2-butyleneoxy group, 2,3-butyleneoxy group, i-butyleneoxy group, pentyleneoxy group, hexyleneoxy group, styryloxy group, decenyloxy group, dodecenyloxy group, tetradecenyloxy group, and hexadecanyloxy group, wherein for t equal to 1 the oxygen atom of the A$_1$ group is bound to the B$_1$ group and the following A$_1$ group is always bound via the oxygen atom to the previous A group;
B$_1$ is independently from each other selected from the group consisting of a bond, linear C$_1$ to C$_{12}$ alkanediyl groups, and branched C$_1$ to C$_{12}$ alkanediyl groups;
R$_4$, R$_8$, and R$_{12}$ being selected from the group consisting of H, linear alkyl, branched alkyl, and cycloalkyl;
Z$_1$ is selected from the group consisting of alanine, arginine, asparagine, aspartic acid, cysteine, glutamine, glycine, histidine, isoleucine, leucine, lysine, methionine, phenylalanine, proline, serine, threonine, tryptophan, tyrosine, valine, and a compound according to Formula (II), wherein said compound according to Formula (II) connects to the compound according to Formula (I) via the bond labeled with *, with the provisio of at least one group R$_4$, R$_8$, and/or R$_{12}$ containing at least 7 or more carbon atoms;

(Formula II)

$$\begin{array}{c} R_{13} \quad R_{14} \quad R_{15} \\ H_2N \diagdown \diagup \diagdown \diagup R_{16} \\ R_{17} \diagup \quad w \quad \diagdown \diagup ^* \\ R_{18} \quad O \end{array}$$

with independently from each other
w being an integer from 0 to 12;
R$_{13}$ and R$_{14}$ independently for each repetition unit w being selected from the group consisting of H, linear alkyl, branched alkyl, and cycloalkyl;
R$_{15}$, R$_{16}$, R$_{17}$, and R$_{18}$ being selected from the group consisting of H, linear alkyl, branched alkyl, and cycloalkyl, comprising the steps of a) Reacting an alcohol according to Formula (III)

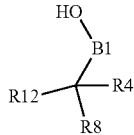

Formula (III)

wherein independently from each other $B_1$ is selected from the group consisting of a bond, linear $C_1$ to $C_{12}$ alkanediyl groups, and branched $C_1$ to $C_{12}$ alkanediyl groups;

$R_4$, $R_8$, and $R_{12}$ being selected from the group consisting of H, linear alkyl, branched alkyl, and cycloalkyl;

with one or more $C_2$ to $C_{16}$ alkylene oxide, followed by b) at least partial esterification of the alkoxylated alcohol with at least one compound selected from the group consisting of alanine, arginine, asparagine, aspartic acid, cysteine, glutamine, glycine, histidine, isoleucine, leucine, lysine, methionine, phenylalanine, proline, serine, threonine, tryptophan, tyrosine, valine, acids according to Formula (IV), and salts thereof,

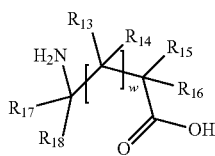

(Formula IV)

with w being an integer from 0 to 12, $R_{13}$ and $R_{14}$ independently for each repetition unit w being selected from the group consisting of H, linear alkyl, branched alkyl, and cycloalkyl;

$R_{15}$, $R_{16}$, $R_{17}$, and $R_{18}$ being selected from the group consisting of H, linear alkyl, branched alkyl, and cycloalkyl.

5. The process according to claim 4, wherein the molar ratio of alcohol according to Formula (III) to total $C_2$ to $C_{12}$ alkylene oxide is in the range of from 1:1 to 1:400.

6. The process according to claim 4, wherein the molar ratio of the acid to the hydroxyl groups of the alkoxylated alcohol is in the range of from 0.1:1 to 1:1.

7. A curing agent for epoxy resins which comprises the esteramine salt according to claim 1.

8. A personal care composition comprising the esteramine salt according to claim 1.

9. The esteramine salt according to claim 1, wherein t is 1 to 10.

10. The esteramine salt according to claim 1, wherein t is 2 to 10.

11. A product which comprises an esteramine of Formula (I) or salt thereof,

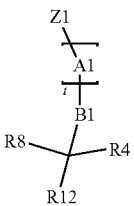

Formula 1 wherein independently from each other t being an integer from 1 to 100;

$A_1$ is independently for each repetition unit t selected from the list consisting of ethyleneoxy group, 1,2-propyleneoxy group, 1,2-butyleneoxy group, 2,3-butyleneoxy group, i-butyleneoxy group, pentyleneoxy group, hexyleneoxy group, styryloxy group, decenyloxy group, dodecenyloxy group, tetradecenyloxy group, and hexadecanyloxy group, wherein for t equal to 1 the oxygen atom of the $A_1$ group is bound to the $B_1$ group and the following $A_1$ group is always bound via the oxygen atom to the previous A group;

$B_1$ is independently from each other selected from the group consisting of a bond, linear $C_1$ to $C_{12}$ alkanediyl groups, and branched $C_1$ to $C_{12}$ alkanediyl groups;

$R_4$, $R_8$, and $R_{12}$ being selected from the group consisting of H, linear alkyl, branched alkyl, and cycloalkyl;

$Z_1$ is selected from the group consisting of alanine, arginine, asparagine, aspartic acid, cysteine, glutamine, glycine, histidine, isoleucine, leucine, lysine, methionine, phenylalanine, proline, serine, threonine, tryptophan, tyrosine, valine, and a compound according to Formula (II), wherein said compound according to Formula (II) connects to the compound according to Formula (I) via the bond labeled with *, with the proviso of at least one group $R_4$, $R_8$, and/or $R_{12}$ containing at least 7 or more carbon atoms;

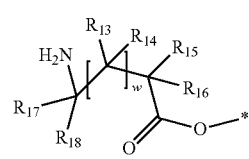

(Formula II)

with independently from each other w being an integer from 0 to 12;

$R_{13}$ and $R_{14}$ independently for each repetition unit w being selected from the group consisting of H, linear alkyl, branched alkyl, and cycloalkyl;

$R_{15}$, $R_{16}$, $R_{17}$, and $R_{18}$ being selected from the group consisting of H, linear alkyl, branched alkyl, and cycloalkyl and wherein the product is a shampoo formulation, a body wash formulation, a liquid laundry detergent formulation, a curing agent for epoxy, a thermoplastic polyamide adhesive, a polyurethane or a polyurea.

12. The product as claimed in claim 11, wherein the product is a polyurethane.

13. The product as claimed in claim 11, wherein the product is a polyurea.

14. The product as claimed in claim 11, wherein the product is a thermoplastic polyamide adhesive.

15. The product as claimed in claim 11, wherein the product is a shampoo or body wash formulation.

16. The product as claimed in claim 11, wherein the product is a liquid laundry detergent formulation.

17. The product as claimed in claim 11, wherein the product is a curing agent for epoxy resins.

* * * * *